United States Patent
Kawabata et al.

(10) Patent No.: US 12,310,790 B2
(45) Date of Patent: May 27, 2025

(54) ACOUSTIC COUPLER AND ULTRASOUND IMAGING METHOD

(71) Applicant: FUJIFILM Corporation, Tokyo (JP)

(72) Inventors: Kenichi Kawabata, Tokyo (JP); Hideki Yoshikawa, Tokyo (JP); Hirozumi Takeshima, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 930 days.

(21) Appl. No.: 17/197,145

(22) Filed: Mar. 10, 2021

(65) Prior Publication Data

US 2021/0282745 A1   Sep. 16, 2021

(30) Foreign Application Priority Data

Mar. 12, 2020 (JP) ................................ 2020-043227

(51) Int. Cl.
  *A61B 8/00* (2006.01)
  *C08F 220/56* (2006.01)
  *C08F 222/38* (2006.01)
  *C08L 5/04* (2006.01)
  *C08L 5/06* (2006.01)

(52) U.S. Cl.
  CPC .......... *A61B 8/4281* (2013.01); *C08F 220/56* (2013.01); *C08F 222/385* (2013.01); *C08L 5/04* (2013.01); *C08L 5/06* (2013.01)

(58) Field of Classification Search
  None
  See application file for complete search history.

(56) References Cited

U.S. PATENT DOCUMENTS

2011/0113886 A1   5/2011   Elejalde et al.

FOREIGN PATENT DOCUMENTS

| JP | 2018-153553 A | 10/2018 |
|----|---------------|---------|
| JP | 2018-175598 A | 11/2018 |
| JP | 2018-195964 A | 12/2018 |
| WO | 2019/039009 A1 | 2/2019 |

OTHER PUBLICATIONS

Chen et al. Soft elastic hydrogel couplants for ultrasonography. 2021 Materials Science and Engineering: C: 119, 111609, 8p. Epub Oct. 9, 2020. (Year: 2021).*
Echo Gel PAD for ultrasound diagnostics, Yasojima Proceed Co., Ltd., 2020, p. 1.
Japanese Office Action received in corresponding Japanese Application No. 2020-043227 dated Sep. 12, 2023.

* cited by examiner

*Primary Examiner* — Jennifer Chin
(74) *Attorney, Agent, or Firm* — MATTINGLY & MALUR, PC

(57) ABSTRACT

Provided is an acoustic coupler capable of achieving both low elastic modulus and high deformability required for ultrasound imaging. The acoustic coupler is disposed between a probe for transmitting ultrasound waves and a subject, the acoustic coupler comprising a hydrogel including a copolymer that contains water. The copolymer comprises a monofunctional monomer having one ethylenically unsaturated group and a polyfunctional monomer having two to six ethylenically unsaturated groups. The molar ratio of the monofunctional monomer to the polyfunctional monomer is more than 90 and less than or equal to 3500.

13 Claims, 11 Drawing Sheets

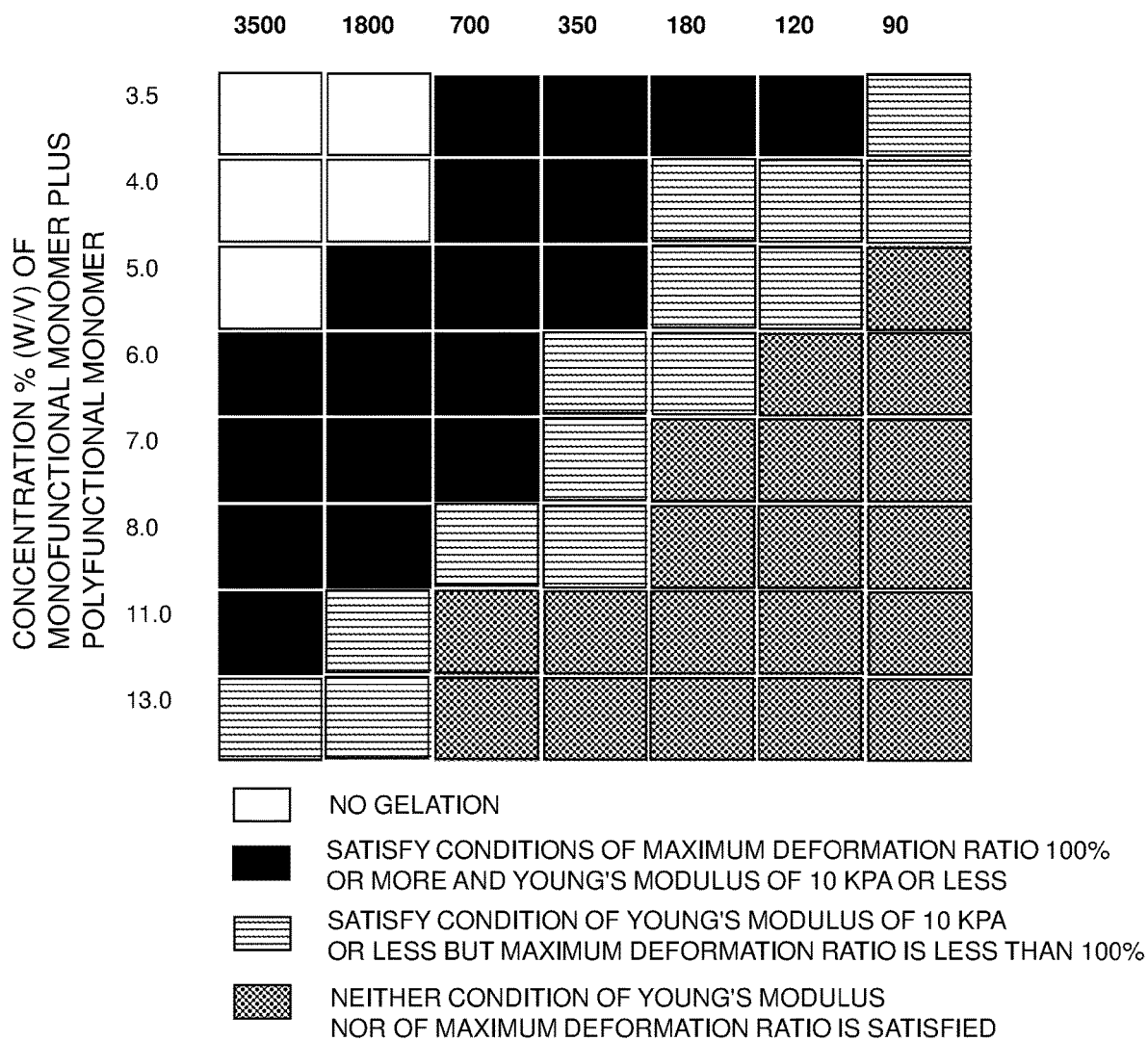

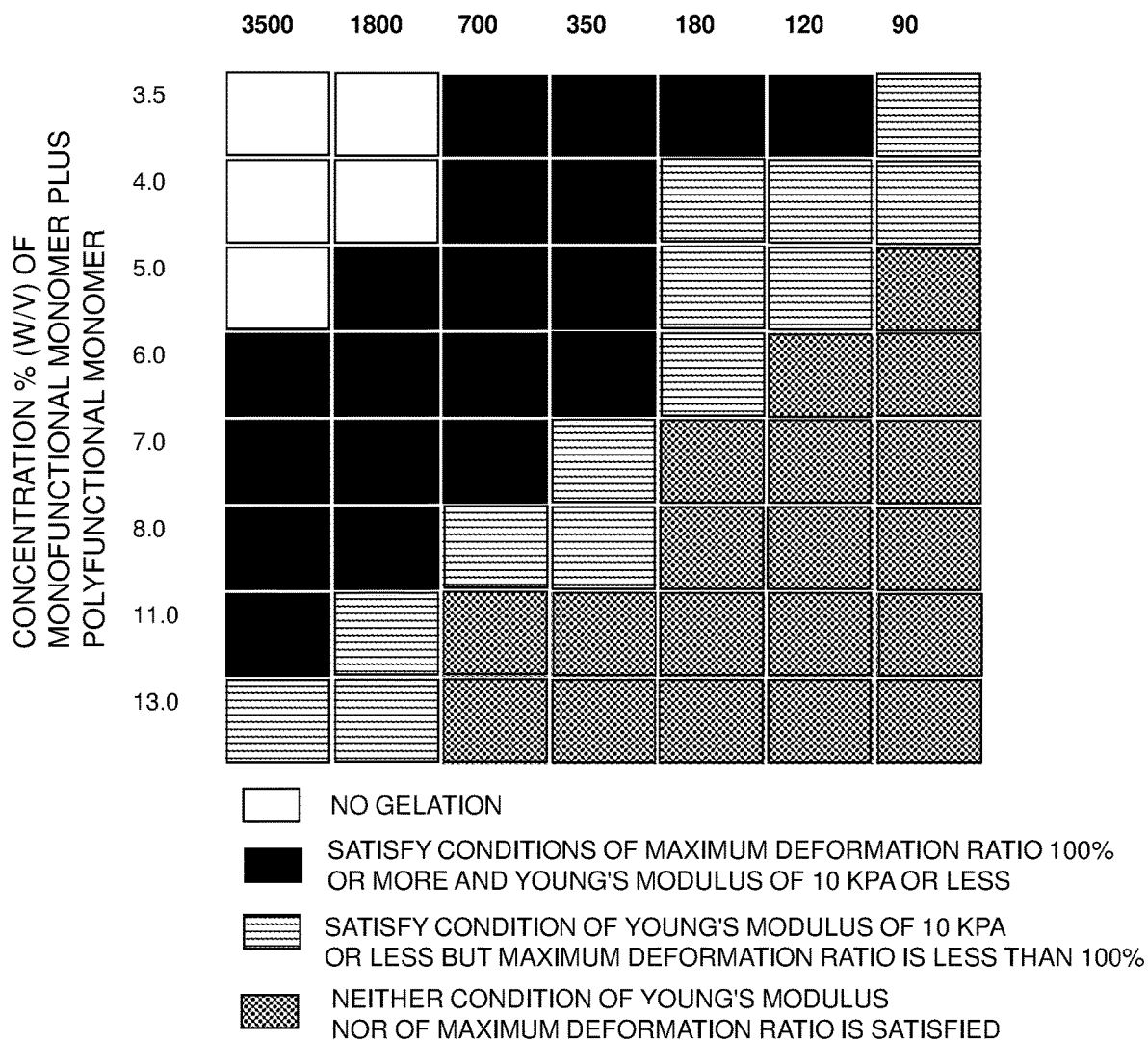

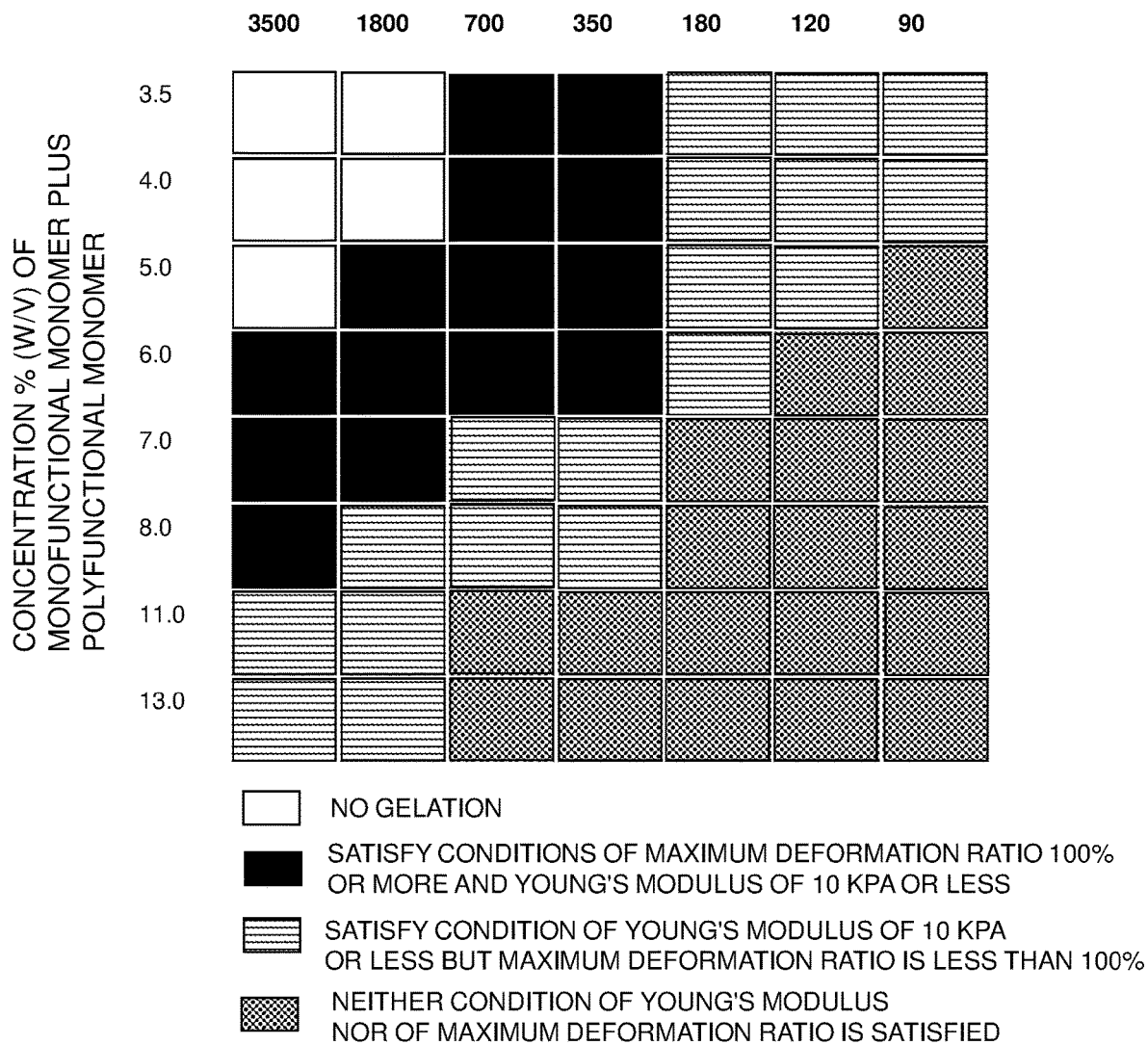

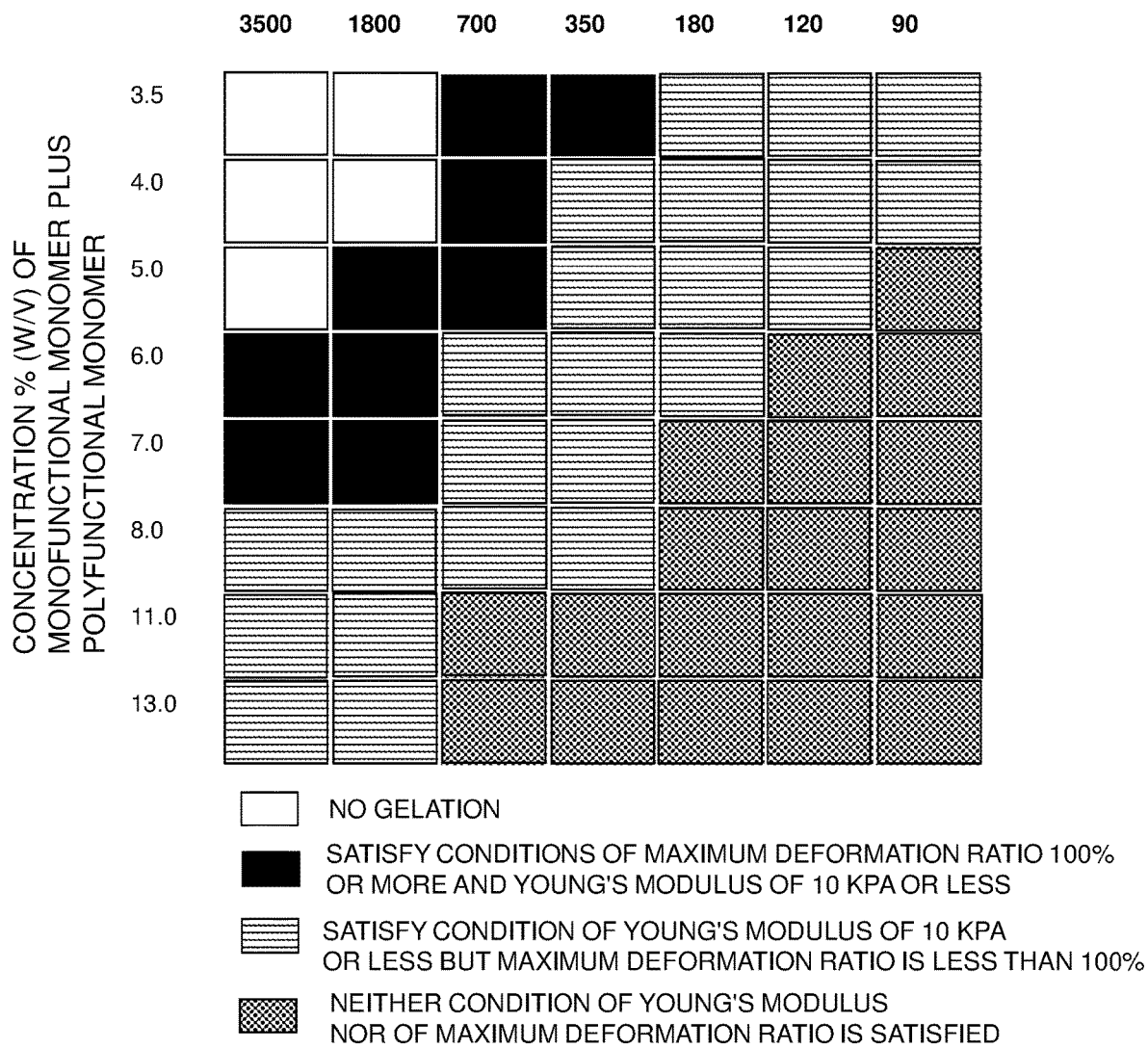

ACOUSTIC COUPLER AND ULTRASOUND IMAGING METHOD

CROSS-REFERENCE TO RELATED APPLICATION

The present application claims priority from Japanese application JP2020-043227, filed on Mar. 12, 2020, the contents of which is hereby incorporated by reference into this application.

BACKGROUND OF THE INVENTION

Field of the Invention

The present invention relates to a coupler for performing acoustic coupling, being disposed between an ultrasound transmitting and receiving probe and an object to be irradiated, to obtain information in a measurement object based on signals acquired by applying ultrasound waves to the measurement object.

Description of the Related Art

In modern medical care, image diagnosis being capable of obtaining inner body information noninvasively is an indispensable technology, and it is widely used. Particularly, in image diagnosis modality, ultrasound diagnostic equipment that can provide solution being small-sized and inexpensive, is highly promising.

In other modalities such as X-ray CT and MRI, an examinee enters the equipment and the whole body is imaged, whereas in the ultrasound diagnostic equipment, body information is acquired in real time by contacting a probe to a position to be imaged of the examinee. Using such an imaging method, while there is an advantage that it is possible to image only a region of interest in detail, imaging skills of an imaging operator, such as the degree and angle when contacting the probe, are directly reflected on the image obtained, and when the imaging operator is changed, a resulting image is also changed, leading to a problem called as "operator dependence".

One of the causes of the operator dependence in imaging by the ultrasound diagnostic equipment is that the way of application of 'jelly' (Japanese general call non-elastic gel in medical ultrasound 'jelly') differs subtly depending on the imaging operator. The probe of the ultrasound diagnostic equipment is pressed against the skin of the examinee and applies ultrasound waves toward the inside of the examinee. On that occasion, body hairs and pores on the surface of the skin of the examinee interfere with the penetrate of ultrasound energy into the examinee. For this reason, the imaging operator applies jelly whose acoustic impedance is close to a living body, between the probe and the skin, to couple the ultrasound probe and the living body, and takes an image by pressing the probe from above the jelly. However, since the jelly is non elastic, it is spread thinly by being pressed by the probe, so that the probe becomes almost in contact with the skin. Therefore, it is not easy to cover non-flat surface of the skin with jelly. Particularly, at a site such as a joint where non-flatness of the living body surface are remarkable, it is difficult to sufficiently fill irregularities on the surface with jelly to smooth them. Thus, a subtle difference in jelly application depending on the imaging operator appears as a significant difference in imaging results.

In addition, when jelly is used in the case where there is a scratch on the skin surface, it is necessary to carefully carry out application and removal after inspection, and thus it is not easy to work efficiency.

In order to solve such problems of jelly as described above, for example, Japanese Unexamined Patent Application Publication Nos. JP-A-2018-195964 and JP-A-2018-175598 (hereinafter, referred to as Patent Documents 1 and 2) have proposed that elastic gel (will be described as gel hereinafter) or resin having the acoustic impedance close to a living body is used as the acoustic coupler.

On the other hand, not only in the medical use but also in industrial use, an ultrasound nondestructive inspection is carried out to detect a defect and others inside an object, by applying ultrasound waves to the object. The ultrasound nondestructive inspection allows an inspection without applying X-rays to the object, and the size of the equipment is small. Therefore, it is used as a convenient technique placing less load on the object. In this ultrasound nondestructive inspection, as in the case of medical use, contact between an ultrasound probe and the object surface may cause a problem depending on the surface shape of the object. For this reason, it is suggested that gel is used as the acoustic coupler in a non-patent document "Echo Gel PAD for ultrasound diagnostics", Yasojima Proceed Co., Ltd., 2020, page 1 (hereinafter, referred to as Non-Patent Document 1).

However, acoustic couplers made of conventional gels or resins have hardly been used in the clinical field. The reason is that such conventional gels and resins do not sufficiently achieve both acoustic properties and mechanical properties required as the acoustic couplers for ultrasound imaging.

Acoustic properties required as the acoustic coupler are to have acoustic characteristics (sound velocity and attenuation) close to those of a living body (nearly water) in order to inject ultrasound waves applied from the probe into the living body.

On the other hand, as the mechanical properties required as the acoustic coupler, it is not destroyed (not cracked) even when pressed against the probe, being deformed to come in close contact with a measurement object, and further, it is important that the acoustic coupler does not deform the surface of the measurement object even when pressing the probe to the measurement object excessively.

The acoustic properties of the acoustic coupler made of gel or resin known until now have high attenuation rate of ultrasound waves, the ultrasound waves attenuating before reaching the depths of the measurement object, and thus it has been difficult to image the deep regions. Therefore, conventional acoustic couplers have only been used in some organizations to image a superficial portion of the measurement object.

In addition, the mechanical properties of the acoustic coupler using conventional gel, particularly hydrogel, have low deformability, and it has been difficult to achieve both hardness and deformability. Therefore, the conventional acoustic couplers have not satisfied the conditions; not destroyed by pressing the probe, deformed in close contact with the measurement object; and moreover, they do not deform the surface of the measurement object.

An object of the present invention is to provide the acoustic coupler that is hardly destroyed, deformed in close contact with the measurement object, and moreover, it does not deform the surface of the measurement object, even when an unskilled person, a robot, or the like, moves the probe.

SUMMARY OF THE INVENTION

In order to achieve the above object, the present invention provides an acoustic coupler disposed between a probe for transmitting ultrasound waves, and a subject, wherein the acoustic coupler includes a hydrogel containing a copolymer that contains water. The copolymer comprises a monofunctional monomer having one ethylenically unsaturated group and a polyfunctional monomer having two to six ethylenically unsaturated groups. The molar ratio of the monofunctional monomer to the polyfunctional monomer is more than 90 and less than or equal to 3500.

The acoustic coupler of the present invention can achieve both a low elastic modulus and high deformability, and thus it is not destroyed but deformed in close contact with the measurement object, regardless of the imaging operator who moves the probe. Moreover, since the acoustic coupler does not deform the surface of the measurement object, it is possible to perform ultrasound imaging with a high image quality.

BRIEF DESCRIPTION OF THE DRAWINGS

FIG. 3 is a graph showing a molar ratio of a monofunctional monomer to a polyfunctional monomer of a raw material solution of the acoustic coupler produced in Example 1, a concentration % (w/v) of the monofunctional monomer (monomer with single functional group) plus the polyfunctional monomer (monomer with multiple functional groups), and further showing whether or not the obtained gel satisfies conditions of a predetermined maximum deformation ratio and a Young's modulus;

FIG. 4 is a graph showing the molar ratio of a monofunctional monomer to a polyfunctional monomer of the raw material solution of the acoustic coupler produced in Example 2, the concentration % (w/v) of the monofunctional monomer plus the polyfunctional monomer, and further showing whether or not the obtained gel satisfies the conditions of the predetermined maximum deformation ratio and the Young's modulus;

FIG. 5 is a graph showing the molar ratio of the monofunctional monomer to the polyfunctional monomer of the raw material solution of the acoustic coupler produced in Example 3, the concentration % (w/v) of the monofunctional monomer plus the polyfunctional monomer, and further showing whether or not the obtained gel satisfies the conditions of the predetermined maximum deformation ratio and the Young's modulus;

FIG. 6 is a graph showing the molar ratio of the monofunctional monomer to the polyfunctional monomer of the raw material solution of the acoustic coupler produced in Example 4, the concentration % (w/v) of the monofunctional monomer plus the polyfunctional monomer, and further showing whether or not the obtained gel satisfies the conditions of the predetermined maximum deformation ratio and the Young's modulus;

DETAILED DESCRIPTION OF THE PREFERRED EMBODIMENTS

Figure 1A:
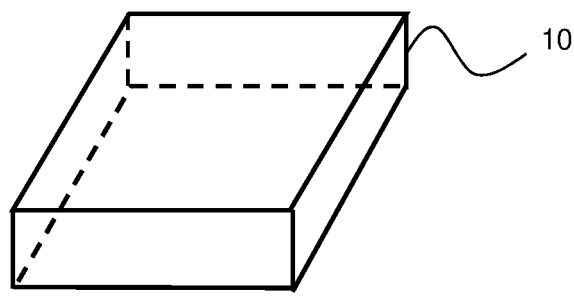
FIG. 1A is a perspective view showing a shape example of an acoustic coupler 10 according to an embodiment of the present invention, and FIG. 1B a perspective view showing the shape example of the acoustic coupler having a structure in which a main gel 11 is supported by a holding member 12 according to an embodiment.

The inventors have conducted extensive studies and have found that a hydrogel having low elastic modulus and high deformability enables an acoustic coupler that achieves both acoustic properties (sound velocity and attenuation) close to water and mechanical properties, not being destroyed (not cracked) even when the probe is pressed, deformed in close contact with a measurement object, and further, not deforming the surface of the measurement object. Specifically, the hydrogel comprises a copolymer containing water, wherein the copolymer comprises a monofunctional monomer having one ethylenically unsaturated group and a polyfunctional monomer having two to six ethylenically unsaturated groups. By setting the ratio of this monofunctional monomer to the polyfunctional monomer in an appropriate range, it is possible to obtain the hydrogel capable of achieving both low elastic modulus and high deformability, which are suitable for use as the acoustic coupler for ultrasound imaging.

For example, when the molar ratio of the monofunctional monomer to the polyfunctional monomer (=monofunctional monomer/polyfunctional monomer) is more than 90 and less than or equal to 3500, the hydrogel enables low elastic modulus and high deformability being required as the acoustic coupler. It is further desirable that the molar ratio should be between or equal to 120 and 3500.

Preferably, the total concentration (weight w/volume v) of the monofunctional monomer having one ethylenically unsaturated group and the polyfunctional monomer having two to six ethylenically unsaturated groups in the raw material solution is more than or equal to 3.5% and less than 13.0%, and more preferably, it is 11.0% or less.

By setting the molar ratio to the ranges as described above, the hydrogel can achieve Young's modulus of 10 kPa or less as the elastic modulus, and the maximum deformation ratio of 100% or more as the high deformability. More preferably, the elastic modulus (Young's modulus) is 5 kPa or less, and the maximum deformation ratio is preferably 200% or more.

The maximum deformation ratio here is obtained by (displacement/initial length), wherein the displacement is obtained by pulling the upper and lower ends of the acoustic coupler upward and downward, respectively, measuring the displacement (=(length in the vertical direction after pulling)−(initial length before pulling)), and then, the maximum value of the displacement after pulled to just before broken is divided by the initial length.

By achieving the Young's modulus of the acoustic coupler being 10 kPa or less, it becomes equivalent to or less than the Young's modulus of a living body, so that even if the acoustic coupler is pressed against the living body by the probe, its surface is hardly deformed. Further, by achieving the maximum deformation ratio being 100% or more, the acoustic coupler is deformed on the surface of the measurement object and brought into close contact with the measurement object, when pressed against the living body by the probe.

Further, since the acoustic coupler of the present embodiment is highly deformable, it can be deformed without destroyed, even when pressed by the probe. Particularly, when the imaging operator is a non-skilled person or in the case of measurement using automatic probe movement such as a robot, a difference in deformation of the measurement object hardly occurs between different sites, and an image quality does not change easily.

For example, as the monofunctional monomer, acrylamide can be used, and as the polyfunctional monomer, N,N'-methylene bis-acrylamide (hereinafter, referred to as bis-acrylamide) can be used.

It should be noted that in the present embodiment, as the monofunctional monomer, one or more selected from (meth)acrylamide, N-methyl(metha)acrylamide, N-ethyl(metha)acrylamide, N-propyl(metha)acrylamide, N,N-dimethyl(metha)acrylamide, and N,N-diethyl(metha)acrylamide, may be used in addition to acrylamide.

Further, as the polyfunctional monomer, in addition to bis-acrylamide, and N,N'-methylenebis(meth)acrylamide N,N'-ethylenebis(meth)acrylamide can also be used. Moreover, both of them may be mixed for use.

A radical polymerization initiator and a radical initiator accelerator may be used, when the monofunctional monomer and the polyfunctional monomer are copolymerized. Any type of the radical polymerization initiator may be used, and for example, APS (ammonium persulfate) or KPS (potassium persulfate) may be used. Further, TEMED (N,N, N',N'-tetramethylethylenediamine) may be used as the radical polymerization accelerator.

In addition, the aforementioned hydrogel being the copolymer comprising the monofunctional monomer having one ethylenically unsaturated group and the polyfunctional monomer having two to six ethylenically unsaturated groups may contain a polysaccharide which performs coordination polymerization by a polyvalent cation ion. In this case, it is desirable that the polysaccharide is contained in concentrations (weight/volume) between or equal to 0.1% and 0.4% based on the volume of the raw material solution. The polysaccharide comprises at least one of alginic acid and pectin. Preferably, this polysaccharide constitutes a gel, and constitutes a double network structure with the hydrogel being the copolymer. Specifically, the hydrogel formed by reacting alginic acid or pectin with a polyvalent metal ion may be used.

As one example of a production method, alginate or pectin is added to the raw material solution before the above-mentioned copolymer is polymerized, and after the copolymer is polymerized, it is immersed in a polyvalent metal ion solution, thereby allowing the alginate or the pectin to gel. This enables a structure of double network gel where a network of the hydrogel being the copolymer of the monofunctional monomer having one ethylenically unsaturated group and the polyfunctional monomer having two to six ethylenically unsaturated groups, is interwound with a network of gels of alginic acid.

In this double network gel, deformation of the hydrogel being the copolymer is supported by another hydrogel (gel of alginic acid or pectin), and thus it is difficult to cause cracking even when a force is applied, and this allows provision of a gel having a large maximum deformation amount.

For example, as the alginate as described above, sodium alginate or potassium alginate may be used. As the polyvalent metal ion, a calcium ion, e.g., a calcium salt solution, may be used.

The hydrogel of the present embodiment is disposed as the acoustic coupler between the probe for transmitting ultrasound waves, and the measurement object, whereby even when the probe is pressed strongly against the measurement object, the acoustic coupler having the maximum deformation ratio of 100% or more is deformed to prevent deformation of the measurement object. Therefore, it is possible to measure the measurement object with a high image quality regardless of the way how the probe is pressed. Further, the acoustic coupler of the present embodiment has a high deformability of the maximum deformation ratio of 100% or more, and thus the acoustic coupler is hardly broken (hardly becomes cracked) even when the probe is pressed thereto.

In addition, in general, the hydrogel being the copolymer obtained by copolymerizing acrylamide contains water, has an acoustic property close to water. Therefore, by using the hydrogel of the present embodiment as the acoustic coupler, it is possible to obtain acoustic properties (sound speed and attenuation) close to water. Thus, the acoustic coupler of the present embodiment allows imaging by ultrasound waves that reach the depth without attenuation, achieving the imaging with reduced operator dependency.

(Ultrasound Imaging Method Using Acoustic Coupler)

There will be described an ultrasound imaging method using the acoustic coupler of the present embodiment.

A gel (acoustic coupler) of the present embodiment is sandwiched between an ultrasound transmission surface of a probe for transmitting ultrasound waves and a measurement object. Alternatively, the periphery of the measurement object is surrounded by the gel, or a subject is placed so as to be embedded in the gel, and the ultrasound transmitting surface of the probe is brought into contact with the outer surface of the gel. In this state, ultrasound waves are transmitted from the probe, passing through the acoustic coupler, to irradiate the subject with the ultrasound waves.

Then, the ultrasound waves from the subject toward the probe can pass through the acoustic coupler and reach the probe for reception. An ultrasound image is generated using ultrasound signals received by the probe.

Thus, influence of unevenness of the subject surface can be reduced by deformation of the acoustic coupler. Moreover, the acoustic coupler allows the ultrasound waves to reach the depth with preventing attenuation, and therefore an ultrasound image with reduced operator dependency can be obtained.

It is desirable that the gel is arranged in such a manner that one surface of the gel is brought into close contact with the surface of the probe for transmitting the ultrasound waves, and the other surface of the gel is brought into close contact with the body surface of the subject. Therefore, it is also possible to form the gel into an appropriate shape in advance according to the imaging site.

For example, in the case of imaging a flat body surface such as a stomach, a pad (flat plate) shaped gel is used, and in the case of imaging a non-flat three-dimensional shape (uneven shape) portion such as a joint of elbow or knee and a breast, it is possible to use a gel which has been molded into a shape to be flat by wrapping the three-dimensional portion.

Since the gel of the present embodiment has an attenuation ratio equivalent to that of water, even when the gel being used has a distribution in thickness, a distribution of attenuation ratios hardly occurs by passing through the gel, and imaging can be performed with reducing an influence due to the uneven shape.

(Shape of Acoustic Coupler)

Since the acoustic coupler of the present invention comprises the hydrogel having excellent deformability as described above, it is possible to change the shape according to its application. Therefore, any shape is applicable. For example, as in FIG. 1A, the hydrogel formed into a rectangular parallelepiped shape can be used as the acoustic coupler 10. The size of the upper surface of the acoustic coupler is only required to be larger than the region where transducers of the probe for transmitting ultrasound waves are arranged (ultrasound transmission surface).

Figure 1B:
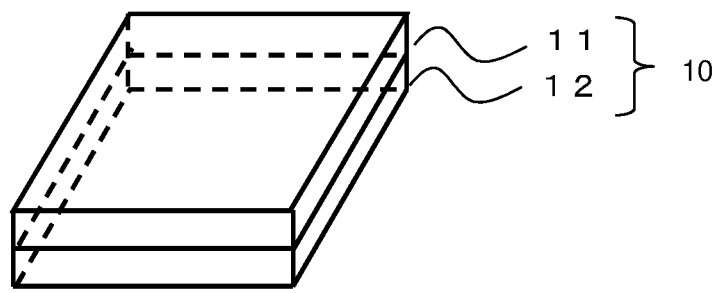

As shown in FIGS. 1B and 2A to 2D, the acoustic coupler of the present invention may be a composite structure where the above-described hydrogel (hereinafter, referred to as main gel) 11 is held by a holding material 12. The main gel 11 is the hydrogel as described above, using a gel having the maximum deformation ratio of 100% or more and Young's modulus of 10 kPa or less. The acoustic coupler as shown in FIG. 1B can provide an acoustic coupler easy to handle, since the main gel can be held by the holding member 12, even when the main gel 11 is too deformable to be handled by itself. For example, the main gel 11 may have high deformability such that when the measurement object is placed on the main gel 11, a part of the measurement object is submerged therein, or the entire measurement object is completely embedded in the main gel 11 by self-weight or the like, so that the outer surface of the measurement object is wrapped by the main gel 11. Even though the main gel 11 has such high deformability, the shape as the acoustic coupler can be maintained by the holding member 12, constituting the easy-to-handle acoustic coupler. Specifically, a gel satisfying a condition of the maximum deformation ratio of 150% or more can be suitably used.

The holding material 12 is provided to efficiently handle the main gel, and any material can be used without restriction for the holding material 12, as far as it does not interfere with acoustic measurement via the main gel 11 and it has a rigidity to the extent that the main gel 11 can be held. For example, a resin, a metallic sheet, a gel having a property smaller in deformability than that of the main gel 11, or the like, can be used as the holding material 12.

Figure 2A:
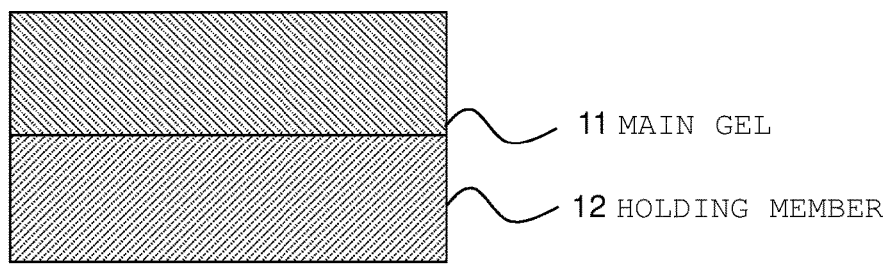
FIGS. 2A to 2D are perspective views showing the shape examples of the acoustic coupler 10 having a structure where the holding member 12 supports the main gel 11 according to an embodiment.
Figure 2B:
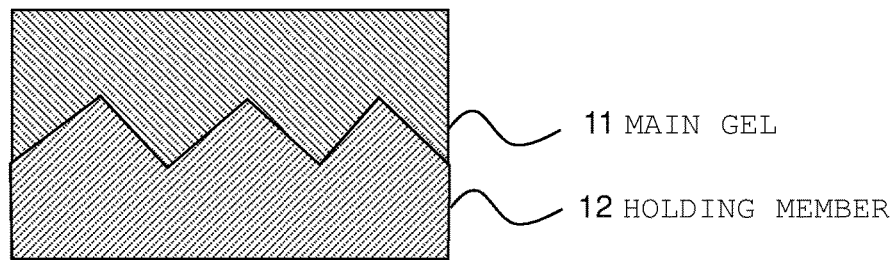

The acoustic coupler of FIGS. 1B, 2A and 2B has a structure where the layer-like main gel 11 is mounted on the upper surface of the layer-like holding member 12. Interface between the holding member 12 and the main gel 11 may be a plane as shown in FIG. 1B and FIG. 2A, or may be provided with the unevenness as in FIG. 2B. In measuring with the structures of FIGS. 1B, 2A and 2B of the acoustic coupler sandwiched between the probe and the measurement object, when the probe is pressed toward the measurement object, the layer of the main gel 11 is deformed and the force of the probe is not transmitted to the measurement object. Therefore, the deformation of the measurement object can be prevented. According to this acoustic coupler, deformation of the main gel 11 can prevent deformation of the measurement object, on any of the sides the main gel 11 is disposed; on the side in contact with the probe and on the side in contact with the measurement object.

Figure 2C:
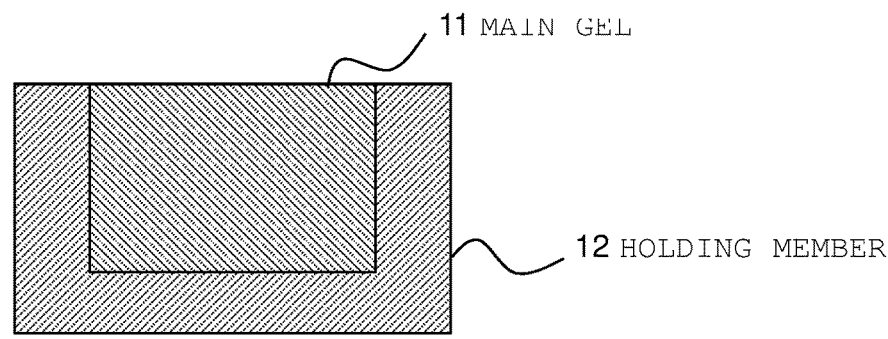

The acoustic coupler of FIG. 2C has a structure where the holding member 12 has a container shape and the main gel 11 is filled inside. The structure of FIG. 2C enables an easy-to-handle acoustic coupler even when the maximum deformation ratio of the main gel 11 is large. Further, mounting the measurement object on the main gel 11 allows the measurement object to be sunk into the main gel 11 or to be surrounded by the main gel. In this state, the probe is brought into contact with the side surface or the lower surface of the holding member 12, and the measurement object can be measured from five directions in total, from four side surfaces and from the lower surface. Further, when the measurement object sinks into the main gel 11, with the upper surface thereof covered by the gel, the measurement can also be performed from the upper surface. Thus, measurement from six directions is possible.

Figure 2D:
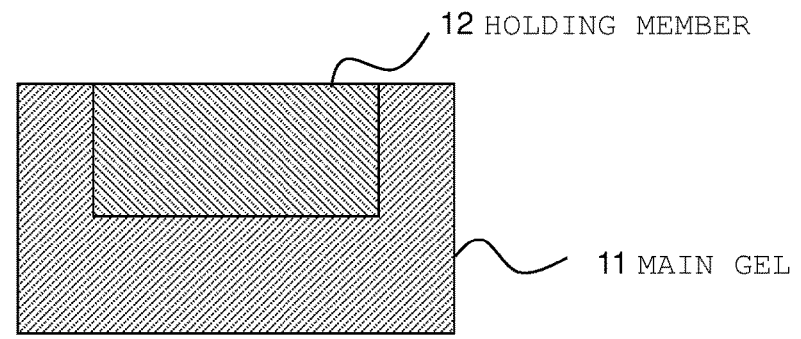

The acoustic coupler of FIG. 2D has a structure where the main gel 11 has the container shape, and the holding member 12 is inserted therein. The structure of FIG. 2D enables an easy-to-handle acoustic coupler even in the case where the maximum deformation ratio of the main gel 11 is large.

In the acoustic coupler having the structures of FIGS. 1B and 2A to 2D, the interface between the main gel 11 and the holding member 12 may be adhered, or it may be a peelable configuration without being adhered.

In addition, in the configurations of FIGS. 1A and 2A to 2D, more than one main gel 11 and more than one holding member 12 may be provided. For example, in the structures of FIGS. 2A to 2D, it is also possible to form a structure where the main gel 11 and the holding material 12 are alternately laminated in multiple layers. The interface between the main gel 11 and the holding material 12 comprising a plurality of laminated layers has a configuration that the main gel is removal from the holding material, and thus the number of the main gels can be adjusted according to the measurement object. For example, the acoustic coupler comprising alternately laminated five layers of the main gel 11 and five layers of the holding member 12 is prepared, and two layers of the main gel 11 and two layers of the holding member 12 may be removed by peeling off, depending on the measurement object. Then, it is possible to obtain the acoustic coupler for measurement use, comprising alternately laminated three layers of the main gel 11 and three layers of the holding member 12.

Further, in the acoustic coupler where a plurality of layers of the main gel 11 and holding member 12 are laminated alternately, it is possible to select as the outermost surface either the main gel 11 or the holding member 12, in association with the measurement object, by peeling off the main gel 11 or the holding member 12 on the outermost surface.

Particularly, when the double network gel is used as the main gel 11, obtained by forming the hydrogel of the copolymer comprising the monofunctional monomer and the polyfunctional monomer with the ethylenically unsaturated groups, followed by immersed in polyvalent metal ion solution to gelate alginic acid, pectin, or the like, it is also possible to use as the holding material 12, a gel obtained by the process; immersed in the polyvalent metal ion solution to gelate alginic acid, pectin, or the like. This allows the main gel 11 and the holding material 12 to be simultaneously obtained as the double network gels. With this configuration, the main gel 11 and the holding material 12 respectively constitute the double network gels with a common gel (the gel such as alginic acid and pectin), and the common gel becomes continuous even on the interface, whereby a bonding property between the main gel 11 and the holding material 12 can be increased.

Further detailed compositions and a method of producing the acoustic coupler using the hydrogel of the present embodiment will be clarified in the following examples.

EXAMPLES

There will now be described examples of the acoustic coupler of the present invention.

Example 1

The hydrogel as the acoustic coupler of Example 1 was produced as follows:

As a raw material, distilled water and a monofunctional monomer having one ethylenically unsaturated group were provided, and these were dissolved at predetermined concentrations to prepare a plurality of raw material solutions.

As shown in FIG. 3, the concentration % (w/v) of the total (weight w) of acrylamide and bis-acrylamide in the raw material solution (volume v) was any of 3.5%, 4.0%, 5.0%, 6.0%, 7.0%, 8.0%, 11.0%, and 13.0%, and the molar ratio of acrylamide to bis-acrylamide (=acrylamide (mol)/bis-acrylamide (mol)) was any of 90, 120, 180, 350, 700, 1800, and 3500, that is, there were prepared 56 types of raw material solutions in total.

Approximately 25 ml of each raw material solution was degassed under reduced pressure for 20 minutes or degassed with nitrogen, and then, APS (ammonium persulfate) and TEMED (N,N,N',N'-tetramethylethylenediamine) were added to the raw material solution so that APS became 0.1% (w/v=(weight w of APS)/(volume v of raw material solution)) and TEMED became 0.05% (v/v=(volume v of TMED)/(volume v of raw material solution)). After the addition, the raw material solution was quickly transferred into a container (60×40×20 mm) and left at an ice temperature for 20 minutes to cause copolymerization between acrylamide and bis-acrylamide to produce the hydrogel.

In this way, 56 types of hydrogels as shown in FIG. 3 were produced where the concentration % (w/v) of the total (weight w) of acrylamide and bis-acrylamide was between or equal to 3.5% and 13.0%, and the molar ratio of acrylamide to bis-acrylamide (=acrylamide (mol)/bis-acrylamide (mol)) was between or equal to 90 and 3500.

Example 2

As the acoustic coupler of Example 2, the following hydrogel was produced.

In the hydrogel of Example 2, sodium alginate was added to the raw material solution to have the concentration of 0.1% (w/v=(weight w of sodium alginate)/(volume v of raw material solution)), and the concentration of the other raw materials and the producing process were made the same as in Example 1 to produce the hydrogel being the copolymer of acrylamide and bis-acrylamide.

Next, thus produced hydrogel being the copolymer was taken out from the container where it was produced, and immersed in 5% calcium chloride solution for 24 hours to impregnate calcium ions, whereby the alginic acid contained in the hydrogel being the copolymer was gelled.

In this way, the hydrogel having the double network was produced, comprising the hydrogel being the copolymer of acrylamide and bis-acrylamide, and the hydrogel of alginic acid. As shown in FIG. 4, the concentration of acrylamide and bis-acrylamide of this gel having the double network, is various in 56 types.

Example 3

As the acoustic coupler of Example 3, the following hydrogel was produced.

In the hydrogel of Example 3, sodium alginate was added to the raw material solution to have the concentration of 0.2% (w/v=(weight w of sodium alginate)/(volume v of raw material solution)), and the concentration of the other raw materials and the producing process were made the same as in Example 2 to produce the 56 types of hydrogels having the double network with different concentrations of acrylamide and bis-acrylamide as in FIG. 5.

Example 4

As the acoustic coupler of Example 4, the following hydrogel was produced.

In the hydrogel of Example 4, sodium alginate was added to the raw material solution to have a concentration of 0.4% (w/v=(weight w of sodium alginate)/(volume v of raw material solution)), and the concentration of the other raw materials and the producing process were made the same as in Example 2 to produce the 56 types of hydrogel having the double network with different concentrations of acrylamide and bis-acrylamide as in FIG. 6.

(Evaluation)
(Measurement of Elastic Modulus and Maximum Deformation Ratio)

The elastic modulus and the maximum deformation ratio of the hydrogels that were produced according to Examples 1 to 4 were measured.

First, the upper end and the lower end of hydrogel sample of each of Examples 1 to 4 were respectively sandwiched by two slides to which an adhesive was applied, whereby the slides were fixed on the upper and lower sides of the sample. The slides above and below the hydrogel sample were secured to fixtures of a tensile tester (any of MX2-500N, ZTA-50N and ZTA-5N of IMADA CO., LTD).

At this stage, the size of the free sample not sandwiched between the slides was 6×1.5×1 cm, the length of the measurement direction (pulling direction=vertical direction) was 1 cm (initial length), and the area in the direction perpendicular to the measurement was 6×1.5 cm (initial area).

In this state, while the sample was pulled vertically at a speed of 100 mm/min, the vertical length of the portion not sandwiched between the slides and the load required for pulling at that time were measured.

An amount of displacement was obtained by subtracting the initial length before pulling from the length of the sample in the vertical direction. The deformation ratio and stress were calculated from the measured displacement and load, and on the basis of these results, the maximum deformation ratio and the elastic modulus (Young's modulus) were calculated as the following.

Figure 7:
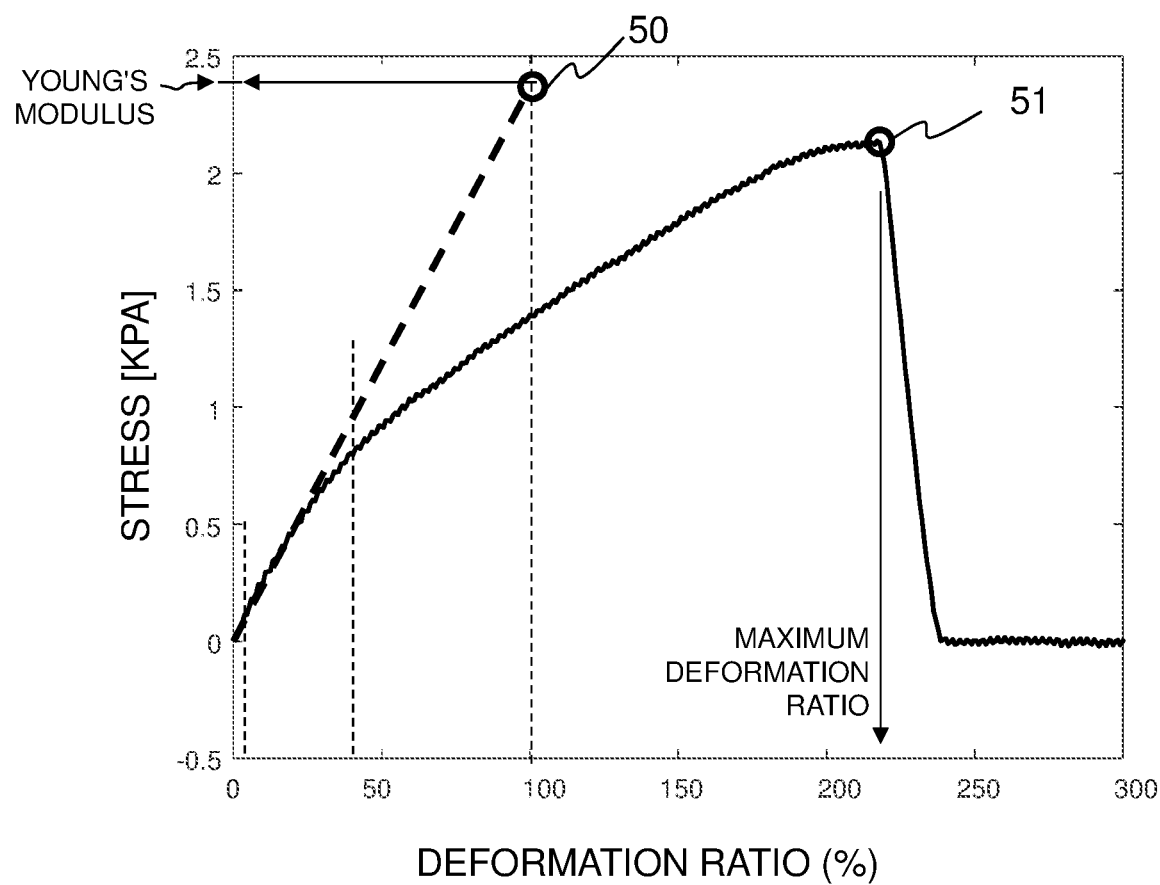
FIG. 7 is a graph showing a measurement method to measure the maximum deformation ratio and the Young's modulus in the embodiments.

The deformation ratio was calculated by dividing the displacement by the initial length. Therefore, for example, if the length of displacement is the same as the initial length, this results in 100% deformation. The stress was calculated by dividing the load during the pulling by the initial area. As shown in FIG. 7, the relationship between thus obtained deformation ratio and the stress was expressed graphically.

In the graph of FIG. 7, a tangent was drawn on the graph using a least squares method in a section where the deformation ratio was in the range from 5 to 40%, and a value of the stress at the point 50 where the tangent reached the deformation ratio of 100% was obtained, and this value was taken as the Young's modulus.

Further, in the graph of FIG. 7, the deformation ratio of the point 51 was assumed as the maximum deformation ratio, where the stress was turned to decrease, after the stress was increased along with increase of the deformation ratio.

Each of FIGS. 3 to 6 shows filling or hatching in the matrix, indicating whether the hydrogel produced in Examples 1 to 4 satisfied the conditions; i.e., even when the hydrogel as the acoustic coupler is pressed against the living body with the probe, the Young's modulus of 10 kPa or less for making the surface difficult to deform, and the maximum deformation ratio of 100% or more allowing the hydrogel to be deformed to be close contact with the surface of the measurement object when the hydrogel is pressed against the living body with the probe. That is, white filling shows that the hydrogel does not gelate, black filling shows both conditions of the maximum deformation ratio and the Young's modulus are satisfied, horizontal line hatching indicates only the Young's modulus condition is satisfied but the condition of the maximum deformation ratio is not satisfied, and dot hatching shows neither the condition of the maximum deformation ratio nor the condition of the Young's modulus is satisfied.

As is apparent from FIG. 3, in the hydrogel of Example 1, both conditions of the maximum deformation ratio of 100% or more and Young's modulus of 10 kPa or less were met in the gels, respectively prepared from the raw material solutions with the total concentration of acrylamide and bis-acrylamide, between or equal to 6% and 11% when the molar ratio of acrylamide to bis-acrylamide was 3500, between or equal to 5% and 8% when the molar ratio was 1800, between or equal to 3.5% and 7% when the molar ratio was 700, between or equal to 3.5% and 5% when the molar ratio was 350, and 3.5% when the molar ratio was 180 and 120.

In addition, as is apparent from FIG. 4, in the hydrogel of Example 2 in which alginic acid was added to the raw material solutions at the concentration of 0.1%, both conditions of the maximum deformation ratio of 100% or more and the Young's modulus of 10 kPa or less were met, in the gels, respectively prepared from the raw material solutions with the total concentration of acrylamide and bis-acrylamide between or equal to 6% and 11% when the molar ratio of acrylamide to bis-acrylamide was 3500, between or equal to 5% and 8% when the molar ratio was 1800, between or equal to 3.5% and 7% when the molar ratio was 700, between or equal to 3.5% and 6% when the molar ratio was 350, and 3.5% when the molar ratio was 180 and 120.

Further, as is apparent from FIG. 5, in the hydrogel of Example 3 in which alginic acid was added to the raw material solution at a concentration of 0.2%, both conditions of the maximum deformation ratio of 100% or more and the Young's modulus of 10 kPa or less were met, in the gels, respectively prepared from the raw material solutions with the total concentration of acrylamide and bis-acrylamide between or equal to 6% and 8% when the molar ratio of acrylamide to bis-acrylamide was 3500, between or equal to 5% and 7% when the molar ratio was 1800, and between or equal to 3.5% and 6% when the molar ratio was 700 and 350.

In addition, as is apparent from FIG. 6, in the hydrogel of Example 4 in which alginic acid was added to the raw material solution at a concentration of 0.4%, both conditions of the maximum deformation ratio of 100% or more and the Young's modulus of 10 kPa or less were met, in the gels, respectively prepared from the raw material solutions with the total concentration of acrylamide and bis-acrylamide between or equal to 6% and 7% when the molar ratio of acrylamide to bis-acrylamide was 3500, between or equal to 5% and 7% when the molar ratio was 1800, between or equal to 3.5% and 5% when the molar ratio was 700, and 3.5% when the molar ratio was 350.

Figure 8:
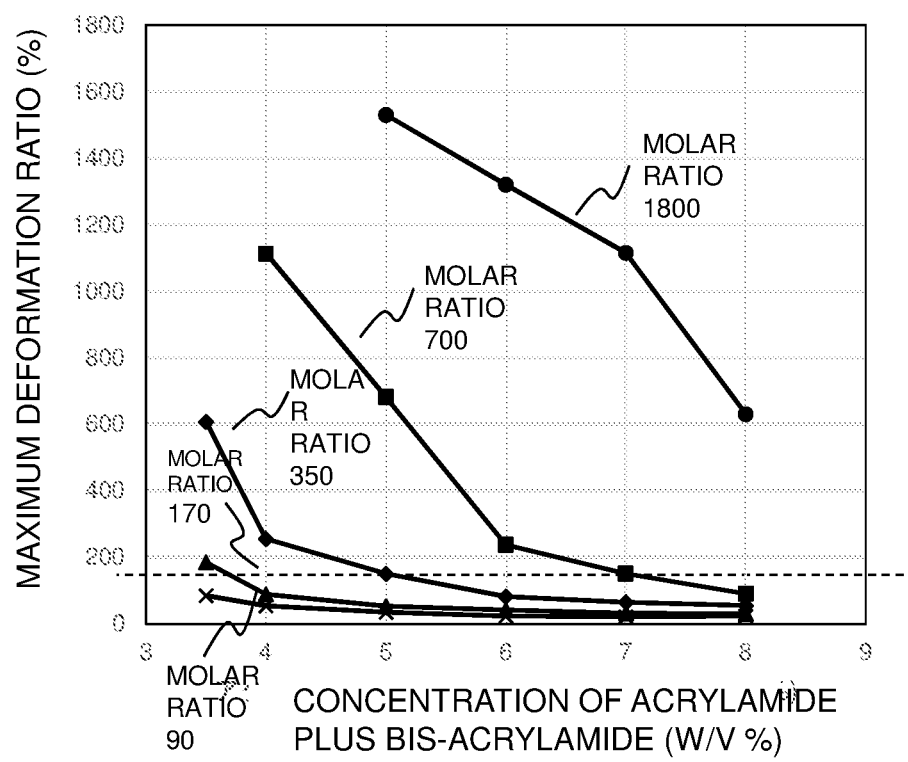
FIG. 8 is a graph showing the relationship between the maximum deformation ratio of the hydrogel produced in Example 1, and total concentration of acrylamide and bis-acrylamide in the raw material solution of the hydrogel.

(Dependence of Maximum Deformation Ratio on Total Concentration of Acrylamide and Bis-Acrylamide) FIG. 8 shows the relationship between the maximum deformation ratio of the hydrogel produced in Example 1, and the total concentration of acrylamide and bis-acrylamide in the raw material solution thereof. In FIG. 8, ● indicates the molar ratio (=acrylamide/bis-acrylamide) of the raw material solution was 1800, and ■ indicates the molar ratio was 700, ◆ indicates the molar ratio was 350, ▲ indicates the molar ratio was 170, and x indicates the molar ratio was 90.

As is apparent from FIG. 8, in general, the maximum deformation ratio tends to increase, as the total concentration of acrylamide and bis-acrylamide becomes lower. In addition, there is a tendency that with the same total concentration, the higher is the molar ratio, the higher is the deformation ratio.

According to FIG. 8, it can be seen that the gels produced from the raw material solution where the total concentration of acrylamide and bis-acrylamide was between or equal to 5% and 8% when the molar ratio (=acrylamide/bis-acrylamide) was 1800, the total concentration was between or equal to 4% and 7% when the molar ratio was 700, the total concentration was between or equal to 3.5% and 5% when the molar ratio was 350, and the total concentration was 3.5% when the molar ratio was 170, satisfies the condition of the Example in which the maximum deformation ratio is 100% or more.

(Dependence of Young's Modulus on the Total Concentration of Acrylamide and Bis-Acrylamide)

Figure 9:
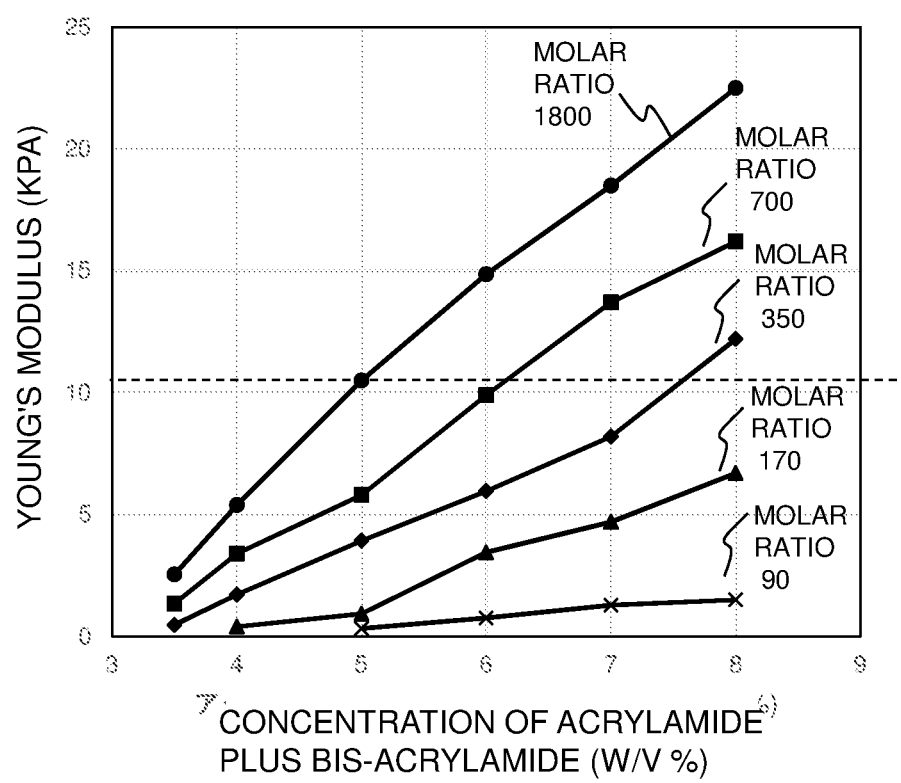
FIG. 9 is a graph showing the relationship between the Young's modulus of the hydrogel produced in Example 1, and the total concentration of acrylamide and bis-acrylamide in the raw material solution of the hydrogel.

FIG. 9 shows the relationship between the Young's modulus of the hydrogel produced in Example 1, and the total concentration of acrylamide and bis-acrylamide in the raw material solution thereof. In FIG. 9, ● indicates the molar ratio (=acrylamide/bis-acrylamide) of the raw material solution was 1800, ■ indicates the molar ratio was 700, ◆ indicates the molar ratio was 350, ▲ indicates the molar ratio was 170, and x indicates the molar ratio was 90.

As is apparent from FIG. 9, in general, the Young's modulus tends to increase as the total concentration of acrylamide and bis-acrylamide increases, and in the same acrylamide concentration, the Young's modulus tends to be higher as the molar ratio becomes higher.

According to FIG. 9, it can be seen that the gels produced from the raw material solutions where the total concentration of acrylamide and bis-acrylamide was between or equal to 3.5% and 4% when the molar ratio (=acrylamide/bis-acrylamide) was 1800, the total concentration was between or equal to 3.5% and 6% when the molar ratio was 700, and the total concentration was between or equal to 3.5% and 7% when the molar ratio was 350, the total concentration was between or equal to 4% and 8% when the molar ratio was 170, and the total concentration was between or equal to 5% and 8% when the molar ratio was 90 satisfies the condition of the Example in which the Young's modulus was 10 kPa or less.

(Dependence of Maximum Deformation Ratio on Total Concentration of Acrylamide and Bis-Acrylamide when Alginic Acid is Added to Raw Material Solution)

Figure 10:
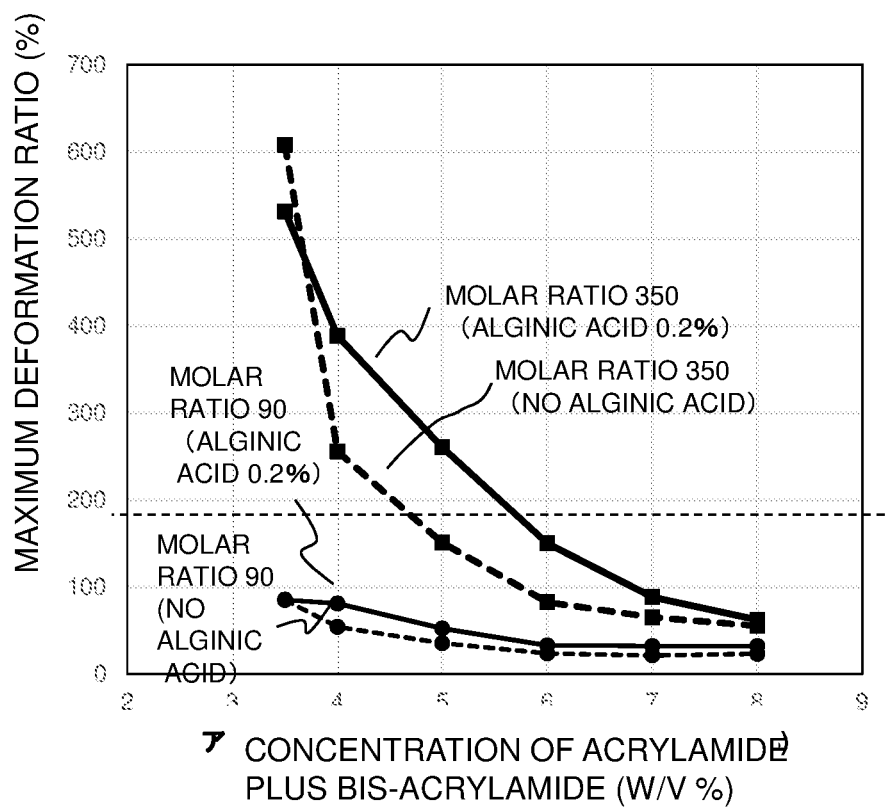
FIG. 10 is a graph showing the relationship between the maximum deformation ratio of the hydrogel, and the total concentration of acrylamide and bis-acrylamide in the raw material solution of the hydrogel, in Example 1 where no alginic acid is added and in Example 3 where alginic acid is added in an amount of 0.2%.

FIG. 10 shows the relationship between the maximum deformation ratio of the hydrogel, and the total concentration of acrylamide and bis-acrylamide in the raw material solution thereof, in Example 1 where no alginic acid was added and in Example 3 where alginic acid was added in an amount of 0.2%.

In FIG. 10, the solid line with ■ indicates the gel obtained from the raw material solution where alginic acid was added in an amount of 0.2% (w/v) at the molar ratio (=acrylamide/bis-acrylamide) of 350 in Example 3, and the dotted line with ■ indicates the gel obtained from the raw material solution at the molar ratio of 350 without containing alginic acid in Example 1. The solid line with ● indicates the gel obtained from the raw material solution where alginic acid was added in an amount of 0.2% (w/v) at the molar ratio of 90 in Example 3, and the dotted line with ● indicates the gel obtained from the raw material solution at the molar ratio of 90 without containing alginic acid in Example 1.

As is apparent from FIG. 10, in the case of the molar ratio of 90, an effect of adding alginic acid was not remarkable, and no difference was found in the maximum deformation ratio regardless whether the alginic acid was added or not.

On the other hand, in the case of the molar ratio of 350, the gel from the raw material solution where the alginic acid was added generally had a higher maximum deformation ratio of the gel. For example, it can be seen that when the total concentration of acrylamide and bis-acrylamide in the raw material solution was 6%, the maximum deformation ratio of the obtained gel was 87% when there was no addition of alginic acid to the raw material solution, and the condition of the maximum deformation ratio of 100% or more of the present embodiment was not satisfied, but when the alginic acid was added in an amount of 0.2%, the maximum deformation ratio was 145%, and the condition of the maximum deformation ratio of the present embodiment was satisfied.

(Dependence of Young's Modulus on the Total Concentration of Acrylamide and Bis-Acrylamide when Alginic Acid is Added to the Raw Solution)

Figure 11:
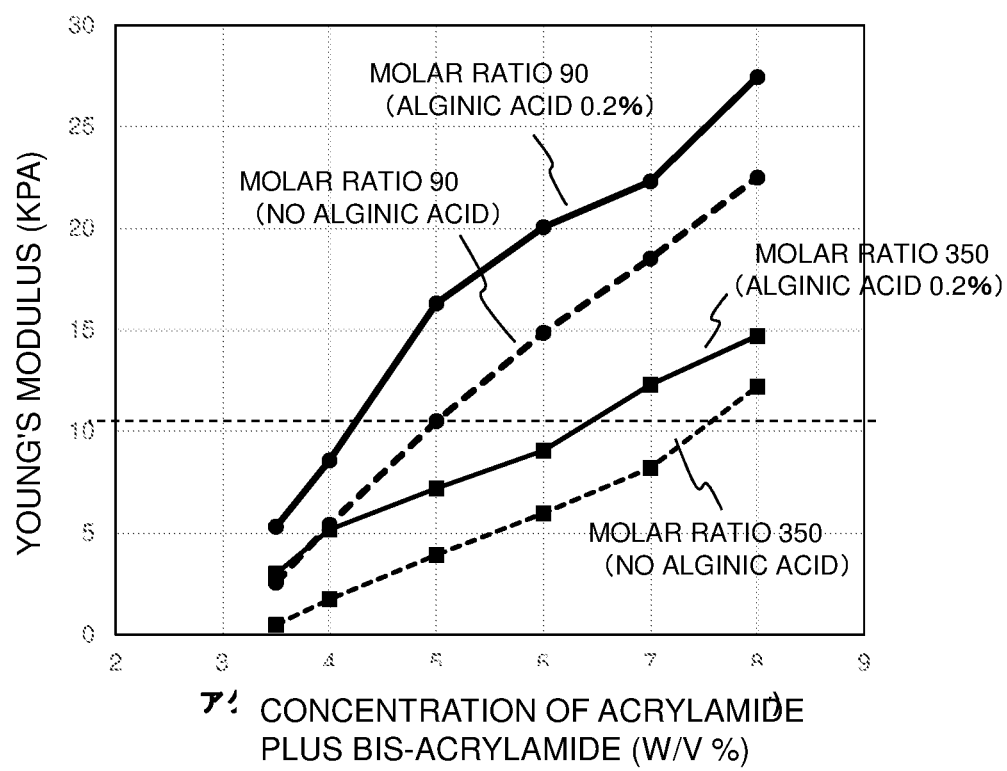
FIG. 11 is a graph showing the relationship between the Young's modulus of the hydrogel, and the total concentration of acrylamide and bis-acrylamide in the raw material solution of the hydrogel, in Example 1 where no alginic acid is added and in Example 3 where alginic acid is added in an amount of 0.2%.

FIG. 11 shows the relationship between the Young's modulus of the hydrogel, and the total concentration of acrylamide and bis-acrylamide in the raw material solution thereof, in Example 1 where no alginic acid was added and in Example 3 where alginic acid was added in an amount of 0.2%.

In FIG. 11, the solid line with ■ indicates the gel obtained from the raw material solution to which alginic acid was added in an amount of 0.2% (w/v) at the molar ratio (=acrylamide/bis-acrylamide) of 350 in Example 3, and the dotted line with ■ indicates the gel obtained from the raw material solution without containing alginic acid at the molar ratio of 350 in Example 1. The solid line with ● indicates the gel obtained from the raw material solution where alginic acid was added in an amount of 0.2% (w/v) at the molar ratio of 90 in Example 3, and the dotted line with ● indicates the gel obtained from the raw material solution without containing alginic acid at the molar ratio of 90 in Example 1. According to FIG. 11, it can be seen, in general, by adding alginic acid, the Young's modulus exhibits a large value. For example, it can be seen in the case of the molar ratio of 90, when the total concentration of acrylamide and bis-acrylamide was 7%, the Young's modulus was 7.7 kPa when no alginic acid was added, and the condition of the Young's modulus of 10 kPa or less of the present embodiment was satisfied, but when alginic acid was added, the Young's modulus was 12.5 kPa, and the condition was not satisfied.

Example 5

As shown in FIG. 1B, the hydrogel as the acoustic coupler of Example 5 was produced where the main gel 11 was held by the holding material 12. It is to be noted the laminated main gels 11 and holding members 12 respectively constitute the double network structures, by the gel of alginic acid which is continuous even on the interface.

First, in Examples 2 to 4, there was prepared the raw material solution containing acrylamide and bis-acrylamide at the molar ratio and the concentration at which a gel having the Young's modulus of 10 kPa or less and the maximum deformation ratio of 100% or more (in the range of black filling in FIGS. 3 to 6) can be obtained, and further containing alginic acid, and according to the method of Example 1, copolymerization was made to occur in a container for producing a composite to produce one-layer hydrogel for the main gel 11.

Next, in Examples 2 to 4, there was prepared the raw material solution containing acrylamide and bis-acrylamide at the molar ratio and the concentration where the gel can be obtained, which does not satisfy the Young's modulus of 10 kPa or less, nor the maximum deformation ratio of 100% or more (in FIGS. 4 to 6, in the range of dot hatching), further containing alginic acid, as the raw material solution for the holding material 12.

The hydrogel of the main gel 11 was placed on the bottom of the container for producing a composite, and the raw material solution for the holding material 12 was poured from above. Then, according to the method of Example 1, copolymerization was made to occur in the container for producing a composite, to produce the hydrogel for the holding material 12 laminated on top of the hydrogel for the main gel 11.

Next, the hydrogel having thus produced two-layered structure was taken out from the container where the hydrogel wad produced, and immersed in the 5% calcium chloride solution for 24 hours to impregnate calcium ions, whereby the alginic acid contained in each of the two-layered hydrogels was gelled.

Thus, in the two-layered hydrogel network, the gel of the alginic acid being continuous even at their interface is formed, making double networks, respectively. Therefore, it was possible to produce a laminate of the main gel 11 and the holding material 12 (FIG. 1B), being the double network gels respectively, each bonded by the gel of alginic acid being continuous at the interface.

What is claimed is:
1. An acoustic coupler, comprising:
a hydrogel having a predetermined three dimensional shape and including a copolymer that contains water, wherein the copolymer is obtained by copolymerizing acrylamide and N,N'-methylenebisacrylamide,
wherein a molar ratio of the acrylamide to the N,N'-methylenebisacrylamide is greater than 90 and less than or equal to 3500,
wherein the hydrogel has a Young's modulus of 10 kPa or less, and
wherein hydrogel has a maximum deformation rate of 100% or more, the maximum deformation rate being a value of a deformation rate obtained by dividing a displacement of a length when a force is applied to the hydrogel by an initial length, the deformation rate being obtained when the force is applied until immediately before the fracture of the hydrogel.

2. The acoustic coupler according to claim 1, wherein the molar ratio is not less than 120 and not greater than 3500.

3. The acoustic coupler according to claim 1, wherein the hydrogel is obtained by copolymerizing the acrylamide and the N, N'-methylenebisacrylamide in a raw material solution in which the acrylamide and the N,N'-methylenebisacrylamide are dissolved in water, wherein a total concentration (weight/volume) of the acrylamide and the N,N'-methylenebisacrylamide with respect to a volume of the raw material solution is more than or equal to 3.5% and less than 13.0%.

4. The acoustic coupler according to claim 3, wherein the total concentration is between or equal to 3.5% and 11.0%.

5. The acoustic coupler according to claim 1, wherein the Young's modulus is of the hydrogel is 5 kPa or less.

6. The acoustic coupler according to claim 1, further comprising a holding member configured to hold the hydrogel.

7. The acoustic coupler according to claim 6, wherein the holding member has a layer structure in contact with the hydrogel.

8. The acoustic coupler according to claim 6, wherein the holding member has a container shape, with a structure that the hydrogel is filled inside the holding member having the container shape.

9. The acoustic coupler according to claim 6, wherein the holding member and the hydrogel have a multi-layer structure.

10. An acoustic coupler, comprising:
a gel having a predetermined three dimensional shape, the gel having the predetermined three dimensional shape being a double network gel in which a hydrogel made of a copolymer containing water and an alginic acid gel obtained by polymerizing alginic acid are entangled, wherein the copolymer comprises: a hydrogel, comprising: a copolymer obtained by copolymerizing acrylamide and N,N'-methylenebisacrylamide,
wherein a molar ratio of the acrylamide to the N,N'-methylenebisacrylamide is greater than 90 and less than or equal to 3500,
wherein the hydrogel has a Young's modulus of 10 kPa or less, and
wherein the hydrogel has a maximum deformation rate of 100% or more, the maximum deformation rate being a value of a deformation rate obtained by dividing a displacement of a length when a force is applied to the hydrogel by an initial length, the deformation rate being obtained when the force is applied until immediately before the fracture of the hydrogel.

11. The acoustic coupler according to claim 10, wherein the alginic acid gel is formed by coordination polymerization of alginic acid with polyvalent cation.

12. The acoustic coupler according to claim 11, wherein the double network gel includes: acrylamide in a raw material solution in which the acrylamide, the N,N'-methylenebisacrylamide, and sodium alginate are dissolved in water,
wherein the N,N'-methylenebisacrylamide is copolymerized, and then sodium alginate is subjected to coordination polymerization by the polyvalent cation, and a total concentration (weight/volume) of the acrylamide and the N,N'-methylenebisacrylamide with respect to a volume of the raw material solution satisfies the acoustic coupler characterized by being less than 13.0% and the concentration (weight/volume) of the sodium alginate to the volume of the aforementioned raw material solution is 0.1% or more and 0.4% or less.

13. The acoustic coupler according to claim 10, further comprising:
a holding material that holds the gel having the predetermined three dimensional shape,
wherein the holding material includes a hydrogel different from a hydrogel of the gel having the predetermined three dimensional shape, and an acoustic coupler comprising a double network gel in which an alginic acid gel obtained by polymerizing alginic acid is entangled, and
wherein the alginic acid gel of the holding material and the alginic acid gel of the gel having the predetermined three dimensional shape are continuous at an interface between the gel having the predetermined three dimensional shape and the holding material.

* * * * *